United States Patent
Bagheri et al.

(10) Patent No.: US 6,680,417 B2
(45) Date of Patent: *Jan. 20, 2004

(54) OLIGOMERIZATION USING A SOLID, UNSUPPORTED METALLOCENE CATALYST SYSTEM

(75) Inventors: Vahid Bagheri, Winfield, IL (US); Robert E. Farritor, Geneva, IL (US); Randall J. Stolk, Naperville, IL (US); Andrew D. Overstreet, Batavia, IL (US); David Eisenberg, Northbrook, IL (US); Frederic Grzeszczak, Brussels (BE)

(73) Assignee: BP Corporation North America Inc., Warrenville, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/037,654

(22) Filed: Jan. 3, 2002

(65) Prior Publication Data

US 2003/0125595 A1 Jul. 3, 2003

(51) Int. Cl.$^7$ .............................. C07C 2/26; C07C 2/32; C07C 2/34

(52) U.S. Cl. ...................... 585/523; 585/521; 585/522; 585/525

(58) Field of Search ................................. 585/523, 522, 585/525, 521

(56) References Cited

U.S. PATENT DOCUMENTS

| | | | |
|---|---|---|---|
| 4,658,078 A | 4/1987 | Slaugh et al. | 585/512 |
| 4,752,597 A | 6/1988 | Turner | 502/104 |
| 4,923,833 A | 5/1990 | Kioka et al. | 502/9 |
| 5,914,376 A | 6/1999 | Herrmann et al. | 526/160 |
| 2001/0041817 A1 * | 11/2001 | Bagheri et al. | 585/517 |
| 2001/0041818 A1 * | 11/2001 | Bagheri et al. | 585/521 |

FOREIGN PATENT DOCUMENTS

| | | | |
|---|---|---|---|
| DE | 19827323 | 12/1999 | C10M/43/08 |
| WO | 0039174 | 7/2000 | C08F/110/06 |

* cited by examiner

*Primary Examiner*—Thuan D. Dang
(74) *Attorney, Agent, or Firm*—James R. Henes

(57) ABSTRACT

A process for the production of an oligomer oil by the polymerization of a feedstock containing one or more $C_3$ to $C_{20}$ 1-olefins in the presence of a solid unsupported metallocene- and activator-containing catalyst system which is formed by removing the solvent from a solution of the soluble metallocene- and activator-containing catalyst system.

43 Claims, No Drawings

OLIGOMERIZATION USING A SOLID, UNSUPPORTED METALLOCENE CATALYST SYSTEM

BACKGROUND OF THE INVENTION

1. Field of the Invention

The present invention relates generally to a process for the polymerization of a feedstock containing one or more $C_3$ to $C_{20}$ 1-olefins in the presence of a solid, unsupported metallocene- and activator-containing catalyst system to form a viscous oligomer oil.

2. Discussion of the Prior Art

Slaugh et al., U.S. Pat. No. 4,658,078 (Apr. 14, 1987), discloses a process for producing relatively low molecular weight dimers by dimerizing alpha olefins to vinylidene olefins by contacting the alpha olefins with a soluble catalyst comprising a metallocene and an aluminoxane. However, the use of a soluble catalyst necessitates a wash step for the removal of catalyst from the polymerization product and the use of a hazardous solvent such as toluene generally required in soluble metallocene catalyst systems. Consequently, efforts have been made to prepare and use heterogeneous or solid metallocene catalyst systems. The solid systems employed have generally involved immobilization of the metallocene and/or aluminium compound serving as the activator on an inorganic support. Such systems suffer from the disadvantage of requiring the use of support material, and are generally of lower activity than soluble catalyst systems.

Consequently, it is highly desirable to be able to prepare and use unsupported solid metallocene catalyst systems with comparable (minimal loss) of catalyst activity. Herrmann et al., U.S. Pat. No. 5,914,376 (Jun. 22, 1999), discloses a process for the polymerization of an olefin in the presence of an unsupported heterogeneous metallocene catalyst system to form a solid polymer. The solid catalyst system is obtained by reacting a soluble metallocene with a solid aluminoxane which is obtained as a by-product obtained in the preparation of toluene-soluble aluminoxanes.

Turner, U.S. Pat. No. 4,752,597 (Jun. 21, 1988) discloses a process for preparing a solid, unsupported matellocene catalyst system. The metallocene catalyst system comprises the metallocene and aluminoxane. The metallocene and aluminoxane are contacted at a mole ratio of aluminoxane to metallocene of from about 12:1 to about 100:1 and reacted in a hydrocarbon solvent in which the metallocene and aluminoxane are each soluble but in which the resulting solid product is insoluble. The metallocene and aluminoxane are reacted at a temperature in the ranges of −78° C. to about 50° C. The resulting solid catalyst is generally sparingly soluble oils at ambient temperature in aromatic solvents, insoluble solids in aliphatic solvents, and decomposes in polar solvents. Upon recovery, the resulting catalyst system was a glassy solid in most of the patent's examples.

Kioka et al., U.S. Pat. No. 4,923,833 (May 8, 1990) discloses five methods for preparing an unsupported solid olefin polymerization catalyst containing a Group IVB metal-containing metallocene component and an aluminoxane component. Three of the methods involve the use of a solvent in which the aluminoxane is insoluble or sparingly soluble. The remaining two methods involve spray drying a solution either of the aluminoxane alone or of the metallocene and aluminoxane together. In Comparative Example 1, the preparation method of the invention is contrasted with a method of preparing an unsupported solid catalyst containing a metallocene and methylaluminoxane by combining a solution of the metallocene in toluene with a solution of methylaluminoxane in toluene and completely evaporating the toluene. Thus, Comparative Example 1 did not employ a solvent in which the methylaluminoxane was only sparingly soluble. The resulting solid catalyst particles had non-uniform shapes, a low specific surface area, and a broad particle size distribution. When used for the polymerization of ethylene to form polyethylene, the comparative catalyst had a substantially lower polymerization activity and resulted in the production of polyethylene having a substantially lower bulk density than when the catalyst of the invention was employed. There is no suggestion or recommendation in U.S. Pat. No. 4,923,833 that the comparative catalyst be used as a polymerization catalyst at all or more particularly as a polymerization catalyst for the production of a viscous oligomer oil.

OBJECTS OF THE INVENTION

It is therefore a general object of the present invention to provide an improved polymerization process employing an unsupported insoluble metallocene catalyst system that overcomes the aforesaid problems of prior art processes.

More particularly, it is an object of the present invention to provide a process for using an unsupported insoluble metallocene catalyst system it in the polymerization of one or more linear $C_3$ to $C_{20}$ 1-olefins to produce a product mixture comprising an essentially terminally unsaturated viscous, essentially 1-olefin poly (1-olefin) or copoly (1-olefin) of molecular weight between about 300 and 10,000 that exhibits a terminal vinylidene content of more than 50%.

Other objects and advantages will become apparent upon reading the following detailed description and appended claims.

SUMMARY OF THE INVENTION

These objects are achieved by the process of the present invention for the production of an oligomer oil comprising:

(i) polymerizing a feed comprising one or more linear $C_3$ to $C_{20}$ 1-olefins having at least one hydrogen on the 2-carbon atom, at least two hydrogens on the 3-carbon atom and at least one hydrogen on the 4-carbon (if at least 4 carbon atoms are present in the olefin), in the presence of a solid metallocene catalyst system comprising a bulky ligand transition metal complex component of the stoichiometric Formula 1 and an activator comprising an organoaluminum compound or a hydrocarbylboron compound or a mixture thereof:

$$L_m MX_n X'_p \qquad \text{Formula 1}$$

wherein L is the bulky ligand, M is the transition metal, X and X' may be the same or different and are independently selected from the group consisting of halogen or a hydrocarbyl group or hydrocarboxyl group having 1–20 carbon atoms, wherein m is 1–3, n is 0–3, p is 0–3 and the sum of the integers m+n+p corresponds to the transition metal valency, to thereby form a viscous oligomer oil product mixture comprising an essentially terminally unsaturated viscous, essentially 1-olefin-containing poly (1-olefin) or copoly (1-olefin) of molecular weight between about 300 and about 10,000 that exhibits a terminal vinylidene content of more than 50%; wherein the aforesaid solid metallocene catalyst system is formed by a process comprising:

(a) combining in an organic solvent boiling below about below 250° C. and a soluble metallocene and a soluble activator comprising at least one of an organoaluminum and a hydrocarbylboron to form a soluble metallocene- and activator-containing catalyst system; and (b) removing the aforesaid solvent to thereby form the aforesaid catalyst system as a solid. The present invention is also the solid metallocene- and activator-containing catalyst system formed by the process of the present invention.

A preferred embodiment the present invention involves producing a viscous oligomer oil having predetermined properties by (ii) oligomerizing at least a pre-selected fraction of the product mixture formed in the aforesaid polymerization step (i) in the presence of an acidic oligomerization catalyst to thereby form the aforesaid oligomer oil, wherein the resulting product mixture comprises less than 35% oligomers that contain two or less monomeric units and at least 60% of oligomers that contain at least three monomeric units.

DETAILED DESCRIPTION OF THE PREFERRED EMBODIMENTS

The metallocene catalyst employed in preparing an unsupported insoluble metallocene catalyst system in step (a) of the method of this invention, comprises a bulky ligand transition metal complex of the stoichiometric Formula 1:

$$L_m M X_n X^1_p \qquad \text{Formula 1}$$

wherein L is the bulky ligand, M is the transition metal, X and $X^1$ are independently selected from the group consisting of halogen, hydrocarbyl group or hydrocarboxyl group having 1–20 carbon atoms, and m is 1–3, n is 0–3, p is 0–3, and the sum of the integers m+n+p corresponds to the transition metal valency. The aforesaid metal complex contains a multiplicity of bonded atoms forming a group which may be cyclic with one or more optional heteroatoms. The ligands L and X may be bridged to each other, and if two ligands L and/or X are present, they may be bridged. The catalyst is a metallocene in which M is a Group IV, V or VI transition metal, and one or more L is a cyclopentadienyl or indenyl moiety.

Preferably, the metallocene is represented by the stoichiometric Formula 2:

$$(Cp)_m M R^1_n R^2_p \qquad \text{Formula 2}$$

wherein each Cp is a substituted or unsubstituted cyclopentadienyl or indenyl ring, and each such substituent thereon can be the same or different and is an alkyl, alkenyl, aryl, alkaryl, or aralkyl radical having from 1 to 20 carbon atoms or at least two carbon atoms formed together to form a part of a $C_4$ or $C_6$ ring; wherein $R^1$ and $R^2$ are independently selected from the group consisting of halogen, hydrocarbyl, hydrocarboxyl, each having 1–20 carbon atoms; and wherein m is 1–3, n is 0–3, p is 0–3, and the sum of m+n+p corresponds to the oxidation state of M.

In alternative preferred embodiments, the metallocene is represented by the stoichiometric Formulas 3 or 4:

$$(C_5 R^3_g)_k R^4_s (C_5 R^3_g) M Q_{3-k-x} \qquad \text{Formula 3}$$

or $$R^4_s (C_5 R^3_g)_2 M Q^1 \qquad \text{Formula 4}$$

wherein each $C_5 R^3_g$ is a substituted or unsubstituted cyclopentadienyl, wherein each $R^3$ may be the same or different and is hydrogen, alkyl, alkenyl, alkaryl or aralkyl having from 1 to 20 carbon atoms or at least 2 carbon atoms joined together to form a part of a $C_4$ to $C_6$ ring; wherein $R^4$ is either 1) an alkylene radical containing from 1 to 4 carbon atoms, or 2) a dialkyl germanium or silicon or an alkyl phosphoric or amine radical, and $R^4$ is substituting on and bridging two $C_5 R^3_g$ rings or bridging one $C_5 R^3_g$ ring back to M, wherein each Q can be the same or different and is an alkyl, alkenyl, aryl, alkaryl, or arylalkyl radical having from 1 to 20 carbon atoms or halogen, and Q' is an alkylidene radical having from 1 to 20 carbon atoms; when k is 0, x is 1, otherwise x is always 0; and wherein s is 0 or 1; and when s is 0, g is 5 and k is 0, 1 or 2; and when s is 1, g is 4 and k is 1. M is a transition metal of Group IV, V or VI, preferably Group IV.

Preferably each $C_5 R^3_g$ is a monosubstituted cyclopentadienyl of the type $C_5 H_4 R^3$ and each $R^3$ may be the same or different and is a primary or secondary alkyl radical. When $R^3$ is a primary alkyl radical, it is preferably methyl, ethyl or n-butyl. When $R^3$ is a secondary radical, it is preferably isopropyl or sec-butyl. The resulting polymerization product has a viscosity in the range of 2–20 cSt at 100° C. In another preferred embodiment, each $C_5 R^3_g$ is a di-, tri-, or tetrasubstituted cyclopentadienyl of the type $C_5 H_3 R^3_2$, $C_5 H_2 R^3_3$ or $C_5 H R^3_4$, and each $R^3$ may be the same or different primary or secondary radical. The resulting polymerization product has a viscosity of 20–5000 cSt at 100° C. In both cases, the reaction is performed at a temperature in the range of from 25 to 150° C.

In addition to the bulky ligand transition metal complex, step (a) of the method of this invention also involves an activating quantity of an activator selected from organoaluminum compounds and hydrocarbylboron compounds. Such organoaluminum compounds include fluoro-organoaluminum compounds. Suitable organoaluminum compounds include compounds of the formula $AlR^{50}_3$, where each $R^{50}$ is independently $C_1$–$C_{12}$ alkyl or halo. Examples include trimethylaluminium (TMA), triethylaluminium (TEA), tri-isobutylaluminium (TIBA), tri-n-octylaluminium, methylaluminiumdichloride, ethylaluminium dichloride, dimethylaluminium chloride, diethylaluminium chloride, ethylaluminumsesquichloride, methylaluminumsesquichloride, and aluminoxanes. Aluminoxanes are well known in the art as typically the oligomeric compounds which can be prepared by the controlled addition of water to an alkylaluminium compound, for example trimethylaluminium. Such compounds can be linear, cyclic or mixtures thereof. Commercially available aluminoxanes are generally believed to be mixtures of linear and cyclic compounds. The cyclic aluminoxanes can be represented by the formula $[R^{51}AlO]_s$ and the linear aluminoxanes by the formula $R^{52}(R^{53}AlO)_s$ wherein s is a number from about 2 to 50, and wherein $R^{51}$, $R^{52}$, and $R^{53}$ represent hydrocarbyl groups, preferably $C_1$ to $C_6$ alkyl groups, for example methyl, ethyl or butyl groups. Alkylaluminoxanes such as linear or cyclic methylaluminoxanes (MAOs) or mixtures thereof are preferred.

Mixtures of aluminoxanes and trialkylaluminium compounds are particularly preferred, such as MAO with TMA or TIBA. In this context it should be noted that the term "aluminoxanes" as used in this specification includes aluminoxanes available commercially which may contain a proportion, typically about 10 weight percent, but optionally up to 50 weight percent, of the corresponding trialkylaluminium, for instance, commercial MAO usually contains approximately 10 weight percent trimethylaluminium (TMA), while commercial MMAO contains both TMA and TIBA. Quantities of aluminoxanes quoted herein include such trialkylaluminium impurities, and accordingly quantities of trialkylaluminium compounds quoted herein are considered to comprise compounds of the formula $AlR_3$ additional to any $AlR_3$ compound incorporated within the alkylalumoxane when present.

Examples of suitable hydrocarbylboron compounds are boroxines, trimethylboron, triethylboron, dimethylphenylammoniumtetra(phenyl)borate, trityltetra(phenyl)borate, triphenylboron, dimethylphenylammonium, tetra(pentafluorophenyl)borate, sodium tetrakis[(bis-3,5-trifluoromethyl)phenyl]borate, trityltetra(pentafluorophenyl)borate and tris(pentafluorophenyl)boron.

In the preparation of the catalysts of the present invention, the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms, of aluminum or boron per atom of the transition metal in the compound of Formula 1. Generally, from about 1 mole to about 5000 moles, preferably at least 150 moles of activator are employed per mole of transition metal complex.

In step (a) of the method of the present invention the metallocene catalyst and activator are combined in a suitable organic solvent at a temperature in the range of from about −40 to 150° C., preferably from about 0 to 100° C. and more preferably from about 20 to 80° C., The metallocene catalyst and activator can initially exist together in the same solution or can initially exist in separate solutions which are then combined. Suitable solvents for use with the metallocene catalyst and/or the activator boil in the range of from −40 to 250° C., preferably from about 0 to 200° C., and most preferably from about 30 to 150° C. at 1 atmosphere pressure. Suitable solvents include C4–C14 aliphatics and monoolefins, light aromatics, alkyl substituted aromatics, halogenated aromatics and aromatic ethers. Preferably the solvent(s) employed include C4–C10 alkanes, C4–C10 mono-olefins, benzene and alkyl substituted benzenes, halogenated aromatics, and aromatic ethers. More preferably the solvent(s) employed include benzene, toluene, xylenes, ethylbenzene, chlorobenzene, C5–C7 alkanes and mono-olefins such as 1-octene and 1-decene. Typically the solvent(s) employed are benzene, toluene, xylenes, and C5–C7 alkanes.

In step (b) of the method of the present invention, the solvent is removed by any convenient conventional technique. Evaporation, optionally under reduced pressure, centrifugation and separation of the liquid from the resulting solid, and spray drying are examples of suitable techniques for converting the dissolved metallocene catalyst and activator to the solid form and separating and recovering the resulting solid from the liquid. Preferably the solid is recovered by evaporation in its dry form.

The solid catalyst system can then be used for polymerization/oligomerization in its solid state, or it can be slurried in a nonvolatile liquid after the aforesaid solvent is removed. Suitable nonvolatile liquids for use as such slurry liquids include C10–C30 hydrocarbons, aromatics with a boiling point between 125° C. and 300° C., halogenated aromatics, and aromatic ethers. Preferably the slurry liquid is a C14 to C24 hydrocarbon.

The polymerization conditions employed in polymerization step (i) of the polymerization/oligomerization method of this invention is slurry phase and either batch, continuous or semi-continuous, with polymerization temperatures ranging from −100° C. to +300° C. In the slurry phase polymerization process, the solid particles of catalyst are fed to a polymerization zone either as dry powder or as a slurry in the polymerization diluent. Preferably, the particles are fed to a polymerization zone as a suspension in the polymerization diluent. The polymerization zone can be, for example, an autoclave or similar reaction vessel, or a continuous loop reactor, e.g. of the type well-known in the manufacture of polyethylene by the Phillips Process.

Step (i) of the present invention can be operated under batch, semi-batch, or so-called "continuous" conditions by methods that are well known in the art. The polymerization process of the step (i) of the method of the present invention is preferably carried out at a temperature above 0° C., more preferably above 15° C. and most preferably in the range of 25–150° C. Adjustment of the polymerization temperature within these defined temperature ranges can provide a useful means of controlling the average molecular weight of the produced polymer. It is also preferred to conduct step (i) under relatively low hydrogen partial pressures, more preferably less than 100 psi and most preferably less than 50 psi.

Monomers that are suitable for use as the olefin that undergoes reaction in step (i) of the process of the present invention are alpha-olefins which have (1) at least one hydrogen on the 2-carbon atom, (2) at least two hydrogens on the 3-carbon atoms, and (3) at least one hydrogen on the 4-carbon (if at least 4 carbon atoms are present in the olefin). Preferably such monomers contain from four to twenty carbon atoms. Thus, suitable alpha-olefin monomers include those represented by the formula $H_2C=CHR^{60}$ wherein $R^{60}$ is a straight chain or branched chain alkyl radical comprising 1 to 18 carbon atoms and wherein any branching that is present is at one or more carbon atoms that are no closer to the double bond than the 4-carbon atoms. $R^{60}$ is an alkyl, preferably containing from 2 to 19 carbon atoms, and more preferably from 2 to 13 atoms. Therefore, useful alpha-olefins include propylene, 1-butene, 1-pentene, 4-methyl-1-pentene, 1-hexene, 1-heptene, 1-octene, 1-nonene, 1-decene, 1-dodecene, 1-tridecene, 1-tetradecene, 1-pentadecene, 1-hexadecene, 1-heptadecene, 1-octadecene, 1-nonadecene and mixtures thereof. Preferably the olefin undergoing reaction contains from four to twenty carbon atoms.

Step (i) of the process of the present invention is controlled to make viscous polymer having a number average molecular weight of not greater than 15,000 and typically from 300 to 10,000, and preferably from 400 to 8,000. The number average molecular weight for such polymers can be determined by any convenient known technique. One convenient method for such determination is by size exclusion chromatography (also known as gel permeation chromatography, GPC) which additionally provides molecular weight distribution information (see W. W. Yau, J. J. Kirkland and D. D. Bly, "Modern Size Exclusion Liquid Chromatography", John Wiley and Sons, New York, 1979). The molecular weight distribution (Mw/Mn) of the polymers or copolymers produced in step (i) is typically less than 5, preferably less than 4, more preferably less than 3, e.g., between 1.5 and 2.5.

The polymers produced in step (i) of this invention are further characterized in that at least about 50% or more of the polymer chains possess terminal ethylenylidene-type unsaturation. A minor amount of the polymer chains can contain terminal vinyl unsaturation, that is, POLY-$CH=CH_2$, and a proportion of the polymers can contain internal monounsaturation, for example, POLY-$C(T^1)=CH$ ($T^2$), wherein $T^1$ and $T^2$ are each independently an alkyl group containing 1 to 18, preferably to 8 carbon atoms and POLY represents the polymer chain. The polymer products of step (i) of this inventive process comprise chains which can be saturated by hydrogen, but preferably contain polymer chains wherein at least 50, preferably at least 60, and more preferably at least 75 percent (e.g., 75–98%), of which exhibit terminal ethenylidene (vinylidene) unsaturation. The percentage of polymer chains exhibiting terminal ethenylidene unsaturation may be determined by Fourier Transform Infrared (FTIR) spectroscopic analysis, titration, proton (H)NMR, or $C^{13}$NMR.

In one preferred embodiment, step (i) is conducted under slurry phase conditions using a catalyst system comprising a catalyst of Formula 2, 3 or 4, in which M is a Group IVb transition metal, typically titanium, zirconium or hafnium, and aluminoxane is an activator with the molar ratio of aluminoxane to metallocene of 150 or greater, and $C_3$–$C_{20}$ alpha-olefins in a feedstock containing more than 1 weight percent of at least one volatile hydrocarbon liquid but consisting essentially of the $C_3$–$C_{20}$ alpha-olefins, are polymerized to form an essentially terminally-unsaturated, viscous, essentially-1-olefin-containing poly(1-olefin) or copoly(1-olefin), having a terminal vinylidene content of more than 50%.

In this preferred embodiment, the terminally unsaturated, viscous polymer product of this invention is essentially a poly(1-olefin) or copoly(1-olefin). The polymer chains of the viscous polymers produced in step (i) of the method of this invention are essentially terminally-unsaturated. By essentially terminally-unsaturated is meant that preferably more than about 90% of the polymer chains contain unsaturation, more preferably more than about 95% of the polymer chains in the product polymer contain terminal unsaturation.

In general, the products produced in step (i) are mixtures whose components and their relative amounts depend upon the particular alpha-olefin reactant, the catalyst and reaction conditions employed. Typically, the products are unsaturated and have viscosities ranging from about 2 to about 5000 cSt at 100° C. At least a portion of the product mixture generally has the desired properties, for example, viscosity, for a particular application. The components in such portion are usually hydrogenated to improve their oxidation resistance and are known for their superior properties of long-life, low volatility, low pour points and high viscosity indices, which make them a premier basestock for state-of-the-art lubricants and hydraulic fluids.

However, usually such product mixture includes substantial amounts of unreacted olefin feed as well as lower oligomers, particularly dimers which do not have the desired properties or do not include the relative amounts of each viscosity product which correspond to market demand. Thus, step (i) is often performed under conditions that are necessary to produce a product mixture that contains an undesired excess or inadequate amount of one product in order to obtain the desired amount of another product.

A preferred embodiment of the process of the present invention solves this problem by fractionating the product mixture produced in polymerization step (i) in order to separate and recover one or more fraction, containing the components having the desired properties and separating one or more other fraction of the product mixture for additional processing in oligomerization step (ii) of the method of this invention. In a less preferred alternative, the entire product from polymerization step (i) can be oligomerized in step (ii).

The fraction(s) selected for additional processing is then subjected to oligomerization conditions in contact with an oligomerization catalyst in step (ii) such that a product mixture containing at least one product having desired properties and in a desired amount that is not produced in step (i). Typically, the low molecular weight fraction, preferably comprising the monomeric and dimeric components thereof, of the product of step (i) is separated and oligomerized in step (ii). In three alternative preferred embodiments, in one case, the monomeric and dimeric components of the product of step (i), in a second case, the dimeric components of the product of step (i) and in a third case, the dimeric and a portion of the trimeric components (with or without monomeric components) of the product of step (i) are separated and oligomerized in step (ii). Thus, oligomerization step (ii) permits the olefin feed to polymerization step (i) to be converted with greater efficiency to desired amounts of products having desired properties. Thus, the method of the present invention permits improved control of the makeup of the feed and permits a wide range of customer specific oligomer oil products to be produced.

For example, the higher molecular weight portion of the product of polymerization step (i) has advantageous properties when compared to products that are currently in the marketplace. To illustrate, when 1-decene is employed as the feedstock to step (i), the higher molecular weight portion of the product of step (i) is primarily $C_{30}$+ and has advantages relative to a polyalphaolefin having a viscosity of 6 cSt or higher because it has a higher viscosity index than the polyalphaolefin having a comparable viscosity.

However, the remaining lower molecular weight portion of the product step (i) is a relatively large volume of low value and lighter oligomeric (primarily dimer and unreacted monomer) fraction. A preferred embodiment of the method of this invention serves to upgrade this lower molecular weight portion of the product of polymerization step (i), which is separated from the aforesaid higher molecular weight portion by any convenient conventional means, for example, distillation, and is then upgraded in oligomerization step (ii). For example, when 1-decene is employed as the feedstock to step (i) and when the portion of the product of step (i) containing 20 carbon atoms and less is employed as the feed or portion of the feed to step (ii), this low molecular weight portion from step (i) is converted in step (ii) to a product mixture in which at least 60%, preferably over 70%, and most preferably over 80% of this crude product mixture contains 30 carbon atoms or greater. The product mixture of step (ii) also contains at most 25%, and preferably not more than 15% of carbon numbers greater than or equal to C50; preferably the product mixture of step (ii) contains less than 25%, and more preferably less than 15% of carbon numbers greater than or equal to C40. The product of step (ii) has sufficiently low volatility, a sufficiently high viscosity index, a desirable viscosity in the range of 4 to 5.5 cSt at 100° C. and less than 5500 cSt at −40° C., and a sufficiently low pour point to serve as base fluids or portions of base fluids for 0W- and 5W- passenger car motor oils and heavy-duty diesel oils. Generally, engine oil formulations and, more particularly 0-W and 5-W engine oil formulations, that comprise at least the fraction of the product mixture of step (ii), at least 60 weight percent of which are oligomers that contain three monomeric units (as defined below), are especially advantageous.

Any suitable oligomerization catalyst known in the art, especially an acidic oligomerization catalyst system, and especially Friedel-Crafts type catalysts such as acid halides (Lewis Acid) or proton acid (Bronsted Acid) catalysts can be employed as the oligomerization catalyst of step (ii). Examples of such oligomerization catalysts include but are not limited to $BF_3$, $BCl_3$, $BBr_3$, sulfuric acid, anhydrous HF, phosphoric acid, polyphosphoric acid, perchloric acid, fluorosulfuric acid, aromatic sulfuric acids, and the like. Like the catalyst employed in step (i), the oligomerization catalyst can be unsupported or supported (absorbed or adsorbed or chemically bound) on a convenient conventional support material. Preferably the oligomerization catalyst is supported. Suitable support materials and their characteristics and impregnation techniques are well known in the art.

Such oligomerization catalysts can be used in combination and with promoters such as water, alcohols, hydrogen halide, alkyl halides and the like. A preferred catalyst system for the oligomerization process of step (ii) is the $BF_3$-promoter catalyst system. Suitable promoters are polar compounds and preferably alcohols containing about 1 to 10 carbon atoms such as methanol, ethanol, isopropanol, n-propanol, n-butanol, isobutanol, n-hexanol, n-octanol and the like. Other suitable promoters include, for example, water, phosphoric acid, fatty acids (e.g., valeric acid) aldehydes, acid anhydrides, ketones, organic esters, ethers, polyhydric alcohols, phenols, ether alcohols and the like. The ethers, esters, acid anhydrides, ketones and aldehydes provide good promotion properties when combined with other promoters which have an active proton e.g. water or alcohols.

Amounts of promoter are used which are effective to provide good conversions in a reasonable time. Generally, amounts of 0.01 weight percent or greater, based on the total amounts of olefin reactants, can be used. Amounts greater than 1.0 weight percent can be used but are not usually necessary. Preferred amounts range from about 0.025 to 0.5 weight percent of the total amount of olefin reactants. Amounts of $BF_3$ are used to provide molar ratios of $BF_3$ to promoter of from about 0.1 to 10:1 and preferably greater than about 1:1. For example, amounts of $BF_3$ of from about 0.1 to 3.0 weight percent of the total amount of olefin reactants are employed.

The amount of catalyst used can be kept to a minimum by bubbling $BF_3$ into an agitated mixture of the olefin reactant only until an "observable" condition is satisfied, i.e. a 2°–4° C. increase in temperature. Because the vinylidene olefins are more reactive than vinyl olefin, less $BF_3$ catalyst is needed compared to the vinyl olefin oligomerization process normally used to produce PAO's.

The high degree of vinylidine type unsaturation of the product of step (i) when catalysts of Formula 2, 3, or 4 are used makes the product very reactive in the oligomerization of step (ii). In addition, since either the entire amount of product of polymerization step (i) or one or more preselected fractions of it can be oligomerized in step (ii), it is possible in the method of this invention to tailor the feedstock to step (ii) in order to produce the desired relative amounts of each viscosity product desired without producing an excess of one product in order to obtain the desired amount of another product which is desired.

A further embodiment of the method of this invention is to co-oligomerize in step (ii) a pre-selected fraction of the product of step (i) with at least one vinyl olefin containing 4 to 20 carbon atoms. This allows for conversion of a fraction of the product of step (i) which may not be useful, for example, the dimer fraction, to a higher fraction, for example, a trimer fraction, which is useful. The addition of a different vinyl olefin than used in polymerization step (i) to the feed of oligomerization step (ii) permits further control of the make-up of the feed to step (ii), and an even wider range of customer specific oligomer oils to be produced. It also allows for production of an oligomer fraction which could not easily be made from other means, for example, co-oligomerizing the $C_{20}$ polymer from step (i) with $C_{12}$ vinyl olefin in step (ii) to form primarily a $C_{32}$ product. In addition, the distribution of products is highly peaked in favor of oligomers having three monomeric units and requires minimal fractionation. The identity of the vinyl olefin employed and the relative amounts of vinyl olefin and aforesaid fraction of the product mixture of step (i) in step (ii) can be varied to control the amount of products formed in step (ii).

Suitable vinyl olefins for use as additional compounds to be added to the feed to step (ii) in the process contain from 4 to about 30 carbon atoms, and, preferably, about 6 to 20 carbon atoms, including mixtures thereof. Non-limiting examples include 1-butene, 1-pentene, 1-hexene, 1-heptene, 1-octene, 1-decene, 1-dodecene, 1-tetradecene, 1-hexadecene, 1-octadecene, 1-eicosene and the like. Pure vinyl olefins or a mixture of vinyl olefins and vinylidene and/or internal olefins can be used. Usually, the feed contains at least about 85 weight percent vinyl olefin. Additionally, step (ii) can be run so that only a fraction of the vinyl olefin reacts with the preselected polymer fraction from step (i).

The oligomerization of step (ii) is very specific for the formation of an oligomer containing three monomeric units. The product mixture formed in step (ii) contains less than 35%, preferably less than 25%, more preferably less than 15% by weight of oligomers that contain two or less monomeric units. The product mixture formed in step (ii) also contains at least 65%, preferably at least 75%, more preferably at least 85% by weight of oligomers that contain three or more monomeric by weight units, and less than 20%, preferably less than 15% more preferably less than 10% of four or more monomeric units. Thus, the product mixture formed in step (ii) generally contains at least 60%, preferably at least 65%, more preferably at least 70%, and most preferably at least 80% by weight of oligomers having three monomeric units.

As employed in this context, the term "monomeric units" is intended to mean both the monomer(s) employed in the feed to polymerization step (i) and the monomer(s) added in oligomerization step (ii) to the portion of the product from step (i) that is employed as the feed to step (ii). Each such monomer can be the source of one or more of the monomeric units that make up an oligomer in the product produced in step (ii). Thus, if no additional vinyl olefinic monomer is added to the portion of the product from step (i) that is employed in the feed to step (ii), the monomers employed in the feed to step (i) are the source of all of the monomeric units in the products formed in step (ii). However, if one or more vinyl olefinic monomers are added to the portion of the product from step (i) that is employed in the feed to step (ii), both such monomers added in step (ii) and the monomers employed in the feed to step (i) are sources of the monomeric units in the products formed in step (ii).

For example, if 1-decene is the feed to step (i) and no other vinyl monomer is added to the feed to step (ii), the oligomers formed in step (ii) and having three monomeric units are trimers of 1-decene. However, if 1-decene is employed as the feed to step (i) and 1-dodecene is added to the feed to step (ii), then the oligomers formed in step (ii) and having three monomeric units have 30, 32, 34 or 36 carbon atoms, with the relative amounts of each depending upon the relative amount of 1-dodecene added.

By varying the choice of the fraction of the product of step (i) that is employed in the feed to step (ii) and of the vinyl olefin added in step (ii), customer-specific oligomer oil products can be produced. For example, the viscosity of such a product can be varied by changing the amount and type of vinyl olefin added to the reaction mixture for the second step. A range of molar ratios of aforesaid pre-selected fraction of the product of step (i) to the vinyl olefin added can be varied, but usually at least a molar equivalent amount of vinyl olefin to the dimeric portion of the aforesaid pre-selected fraction of the product of step (i) is used in order to consume the dimeric portions of the aforesaid pre-selected fraction of the product of step (i). The product oils have viscosities of from about 1 to 20 cSt at 100° C. Preferably, mole ratios of from about 10:1 to 1:1.5 and most typically about 1.3:1 of the added vinyl olefin to the aforesaid pre-selected fraction of the product of step (i) are used for the feed to step (ii). The vinyl olefin is typically added at a time when at least about 30 percent by weight of the aforesaid pre-selected fraction of the product of step (i) has been oligomerized in step (ii).

Oligomerization step (ii) can be carried out at atmospheric pressure. Moderately elevated pressures, e.g. to 50 pounds per square inch, can be used and may be desirable to minimize reaction time but are not necessary because of the high reactivity of the vinylidene olefin. Reaction times and temperatures in step (ii) are chosen to efficiently obtain good conversions to the desired product. Generally, temperatures of from about 0° to 70° C. are used with total reaction times of from about 15 minutes to 5 hours.

The products from step (ii) of the method of the present invention do have the pre-selected desired properties, especially viscosity. Typically, the products of step (ii) are characterized, following removal of unreacted monomer and dimer, by having a viscosity between 3 and 100 cSt, a viscosity index between 110 and 180, a pour point less than −30° C., and a Noack volatility at 250° C. between 2% and 25%.

When the polymerization step (i) is terminated, the solid catalyst system and liquid product mixture are separated by any convenient conventional solid-liquid separation technique such as filtration, centrifugation, or settling and decantation. The separated viscous oligomer product is recovered essentially free of contamination by residual amounts of catalyst. The separated solid catalysts system can be re-used in a subsequent polymerization step (ii).

The following examples will serve to illustrate certain specific embodiments of the invention disclosed herein. These examples are for illustrative purposes only and should not be construed as limiting the scope of the novel invention disclosed herein as there are many alternative modifications and variations which will be apparent to those skilled in the art and which fall within the scope and spirit of the disclosed invention.

EXAMPLES 1–12

All manipulations in Examples 1–10 with the metallocenes and other organometallic compounds were carried out in a glove box under nitrogen. Determination of the amount of terminal vinylidene in a fluid sample was made using NMR by integration of the peak area in the olefinic regions. Molecular weights were determined using gel permeation chromatography (GPC). Trace metal analysis (elemental analysis) were conducted by the inductively coupled plasma (ICP) method. All viscometric properties were measured using appropriate ASTM methods.

Example 1

A 500-mL round bottom flask under nitrogen was charged sequentially with a solution of 81.4 mg of bis (cyclopentadienyl)zirconium dichloride in 20 mL of toluene followed by the addition of 85.6 mL of a solution of methylaluminoxane (MAO) in toluene (10 wt % in toluene, d=0.88 g/mL, 4.52 wt % Al) which resulted in the formation of totally homogeneous yellow solution (molar ratio of Al/metallocene of about 450). Solvent and volatiles including trimethylaluminum were removed under reduced pressure (0.1 mm Hg) for 3 hours at temperature of 35–40° C. resulting in the formation of 6.73 g of a yellow solid powder.

Example 2

A 500-mL round bottom flask under nitrogen was charged sequentially with a solution of 40.7 mg of bis (cyclopentadienyl)zirconium dichloride in 20 mL of toluene followed by the addition of 85.6 mL of a solution of methylaluminoxane (MAO) in toluene (10 wt % in toluene, d=0.88 g/mL, 4.52 wt % Al) which resulted in the formation of totally homogeneous yellow solution (molar ratio of Al/metallocene of about 900). Solvent and volatiles including trimethylaluminum were removed under reduced pressure (0.1 mm Hg) for 3 hours at temperature of 35–40° C. resulting in the formation of 6.86 g of a yellow solid powder.

Example 3

A 500-mL round bottom flask under nitrogen was charged sequentially with a solution of 81.4 mg of bis (cyclopentadienyl)zirconium dichloride in 20 mL of toluene followed by the addition of 57.0 mL of a solution of methylaluminoxane (MAO) in toluene (10 wt % in toluene, d=0.88 g/mL, 4.52 wt % Al) which resulted in the formation of totally homogeneous yellow solution (molar ratio of Al/metallocene of about 300). Solvent and volatiles including trimethylaluminum were removed under reduced pressure (0.1 mm Hg) for 3 hours at temperature of 35–40° C. resulting in the formation of 4.48 g of a yellow solid powder.

Example 4

In a dry box, a 1-liter Parr reactor under nitrogen was charged with 500 mL of dry 1-decene followed by the addition of 0.32 g of the solid catalyst prepared according to the procedure of Example 1. The mixture was stirred at 40° C. for 3 hours. The reaction content was filtered through a 33 g cake of Celite 545 resulting in isolation of clear fluid. Removal of unreacted decene under reduced pressure resulted in isolation of 166.3 g of a clear fluid. Further distillation of this fluid under reduced pressure resulted in isolation of 8.15 g (4.9%) of the dimeric C20 fluid having greater than 80% vinylidene by NMR analysis. Once the dimer was removed by distillation, the bottom fraction showed a measured viscosity of 97.7 cSt, KV @ 100° C. It was further analyzed by ICP having an Al content of 0.3 ppm and a Zr content of <0.09 ppm. This fluid can be further hydrogenated under standard hydrogenation conditions to improve its stability for a variety of applications such as synthetic basestocks for lubricant applications.

Example 5

In a dry box, a 1-liter Parr reactor under nitrogen was charged with 500 mL of dry 1-decene followed by the addition of 0.64 g of the solid catalyst prepared according to the procedure of Example 2. The mixture was stirred at 40° C. for 3 hours. The reaction content was filtered through a 33 g cake of Celite 545 resulting in isolation of clear fluid. Removal of unreacted decene under reduced pressure resulted in isolation of 196.3 g of a clear fluid. Further distillation of this fluid under reduced pressure resulted in isolation of 8.05 g (4.1%) of the dimeric C20 fluid having greater than 80% vinylidene by NMR analysis. Once the dimer was removed by distillation, the bottom fraction showed a measured viscosity of 79.4 cSt, KV @ 100° C. It was further analyzed by ICP having an Al content of 1.03 ppm and a Zr content of <0.08 ppm. This fluid can be further hydrogenated under standard hydrogenation conditions to improve its stability for a variety of applications such as synthetic basestocks for lubricant applications.

Example 6

In a dry box, a 1-liter Parr reactor under nitrogen was charged with 500 mL of dry 1-decene followed by the addition of 0.21 g of the solid catalyst prepared according to the procedure of Example 3. The mixture was stirred at 40° C. for 3 hours. The reaction content was filtered through a 33 g cake of Celite 545 resulting in isolation of clear fluid. Removal of unreacted decene under reduced pressure resulted in isolation of 85.7 g of a clear fluid. Further distillation of this fluid under reduced pressure resulted in isolation of 7.28 g (8.5%) of the dimeric C20 fluid having greater than 80% vinylidene by NMR analysis. Once the dimer was removed by distillation, the bottom fraction showed a measured viscosity of 76.4 cSt, KV @ 100° C. This fluid can be further hydrogenated under standard hydrogenation conditions to improve its stability for a variety of applications such as synthetic basestocks for lubricant applications.

Example 7

In a dry box, a 1-liter Parr reactor under nitrogen was charged with 500 mL of dry 1-decene followed by the addition of 0.32 g of the solid catalyst prepared according to the procedure of Example 1. The mixture was stirred at 60° C. for 3 hours. The reaction content was filtered through a 33 g cake of Celite 545 resulting in isolation of clear fluid. Removal of unreacted decene under reduced pressure resulted in isolation of 143.5 g of a clear fluid. Further distillation of this fluid under reduced pressure resulted in isolation of 20.23 g (14.1%) of the dimeric C20 fluid having greater than 80% vinylidene by NMR analysis. Once the dimer was removed by distillation, the bottom fraction showed a measured viscosity of 37.5 cSt, KV @ 100° C. It was further analyzed by ICP having an Al content of <0.1 ppm and a Zr content of <0.06 ppm. This fluid can be further hydrogenated under standard hydrogenation conditions to improve its stability for a variety of applications such as synthetic basestocks for lubricant applications.

Example 8

In a dry box, a 1-liter Parr reactor under nitrogen was charged with 500 mL of dry 1-decene followed by the addition of 0.50 ml of triisobutylaluminum and stirred for 10 minutes. The reaction content was treated with 0.32 g of the solid catalyst prepared according to the procedure of Example 1 and it was stirred at 60° C. for 3 hours. The reaction was quenched and extracted by the addition of 200 ml of 2 N NaOH followed by washing of the organic layer with 200 ml of water. Removal of unreacted decene under reduced pressure resulted in isolation of 208.4 g of a completely clear fluid. Further distillation of this fluid under reduced pressure resulted in isolation of 23.3 g (11.2%) of the dimeric C20 fluid having greater than 80% vinylidene by NMR analysis. Once the dimer was removed by distillation, the clear bottom fraction (free of trace metals) showed a measured viscosity of 57.3 cSt, KV @ 100° C. This fluid can be further hydrogenated under standard hydrogenation conditions to improve its stability for a variety of applications such as synthetic basestocks for lubricant applications.

Example 9

In a dry box, a 1-liter Parr reactor under nitrogen was charged with 500 mL of dry 1-decene followed by the addition of 0.32 g of the solid catalyst prepared according to the procedure of Example 1. The mixture was stirred at 95° C. for 3 hours. The reaction was quenched and extracted by the addition of 200 ml of 2 N NaOH followed by washing of the organic layer with 200 ml of water. Removal of unreacted decene under reduced pressure resulted in isolation of 101.7 g of a completely clear fluid. Further distillation of this fluid under reduced pressure resulted in isolation of 35.3 g (34.7%) of the dimeric C20 fluid having greater than 80% vinylidene by NMR analysis. Once the dimer was removed by distillation, the clear bottom fraction (free of trace metals) showed a measured viscosity of 13.7 cSt, KV @ 100° C. This fluid can be further hydrogenated under standard hydrogenation conditions to improve its stability for a variety of applications such as synthetic basestocks for lubricant applications.

Example 10

A 1-gallon Parr reactor is charged with 643.0 g of the C20 dimeric fluid isolated from a large scale version of Examples 9, 357.0 g 1-decene, 2.0 g 1-butanol and is taken to 50° C. with stirring. Boron trifluoride is introduced and it is adjusted slowly to a steady state pressure of 20 psi. The reaction mixture is stirred for 90 minutes. The reaction mixture is quenched with 500 g of 8% NaOH and is washed with distilled water. Removal of unreacted and volatile fluids under reduced pressure (200° C., 0.05 mmHg) results in isolation of 804.7 g of a clear fluid which is further hydrogenated under a set of standard hydrogenation conditions (at 170° C., 400 psi hydrogen, using Ni on Kieselguhr catalyst) to produce a high viscosity index (VI) synthetic basestock having the following properties:

| | |
|---|---|
| KV @ 100° C., cSt | 4.3 |
| KV @ 40° C., cSt | 19.4 |
| KV @ −40° C., cSt | 2942 |
| Viscosity Index (VI) | 134 |
| Pour Point, C. | <−66 |
| Noack @ 250, % Loss | 10.3 |

GC Results

After 90 min crude is about: 4% unreacted C10, 9% C20, 65% C30, 16% C40, 3% C50

Example 11

A 1-gallon Parr reactor is charged with 651.2 g of the C20 dimeric fluid isolated from a large scale version of Examples 9, 400.1 g 1-dodecene, 1.0 g 1-propanol and is taken to 45° C. with stirring. Boron trifluoride is introduced and it is adjusted slowly to a steady state pressure of 20 psi. The reaction mixture is stirred for 2 hours. The reaction mixture is quenched with 500 g of 8% NaOH and is washed with distilled water. Removal of unreacted and volatile fluids under reduced pressure (230° C., 0.05 mmHg) results in isolation of 870.2 g of a clear fluid which is further hydrogenated under a set of standard hydrogenation conditions (at 170° C., 400 psi hydrogen, using Ni on Kieselguhr catalyst)

to produce a high viscosity index (VI) synthetic basestock having the following properties:

| | |
|---|---|
| KV @ 100° C., cSt | 4.7 |
| KV @ 40° C., cSt | 21.8 |
| KV @ −40° C., cSt | 3870 |
| Viscosity Index (VI) | 141 |
| Pour Point, C. | <−63 |
| Noack @ 250, % Loss | 7.1 |

GC Results

After 2h crude is about: 4% unreacted C12, 4% C20, 2% C24, 64% C32, 19% C36, balance C40+.

After distillation about: 1% C20, 2% C24, 65% C32, 16% C36, balance C40+

Example 12-Comparative

In a dry box, a 1-liter Parr reactor under nitrogen was charged with 500 mL of dry 1-decene followed by the addition of a homogenous catalyst system prepared separately by pre-mixing for 10 minutes a solution of 3.8 mg of bis(cyclopentadienyl)zirconium dichloride in 20 mL of toluene with 8.0 mL of a solution of methylaluminoxane (MAO) in toluene (10 wt % in toluene, d=0.88 g/mL, 4.52 wt % Al which resulted in the formation of totally homogeneous yellow solution having molar ratio of Al/metallocene of about 450). The reaction mixture was stirred at 40° C. for 3 hours. The reaction content was filtered through a 33 g cake of Celite 545 resulting in isolation of a hazy/cloudy fluid indicating incomplete removal of catalyst residues. Removal of unreacted decene under reduced pressure resulted in isolation of 187.6 g of a hazy/cloudy fluid. Further distillation of this fluid under reduced pressure resulted in isolation of 8.07 g (4.3%) of the dimeric C20 fluid having greater than 80% vinylidene by NMR analysis. Once the dimer was removed by distillation, the hazy bottom fraction showed a measured viscosity of 59.8 cSt, KV @ 100° C. It was further analyzed by ICP having an Al content of 126 ppm and a Zr content of 0.53 ppm. Elemental analysis (ICP) indicates that filtration (through Celite) is not an effective method for removing catalyst residues from the product for the homogenous catalyst system as it showed significantly higher content of Al and Zr metals when compared to the solid/heterogeneous catalyst system under otherwise identical conditions.

Comparison of Examples 4 and 12 illustrates that the only difference between their procedures is that a solid unsupported polymerization catalyst system employed in the present invention is employed in Example 4 while a soluble polymerization catalyst system is employed in Example 12. The polymer yields for the two examples are very similar and within experimental error indicating that the solid unsupported catalyst system employed in the present invention has approximately the same activity as the homogeneous catalyst.

From the above description, it is apparent that the objects of the present invention have been achieved. While only certain embodiments have been set forth, alternative embodiments and various modifications will be apparent from the above description to those skilled in the art. The alternatives are considered equivalents and within the spirit and scope of the present invention, Having described the invention what is claimed is:

1. A process for the production of a viscous oligomer oil having predetermined properties comprising:

(i) polymerizing a feed comprising one or more linear $C_3$ to $C_{20}$ olefins having at least one hydrogen on the 2-carbon atom, at least two hydrogens on the 3-carbon atom and at least one hydrogen on the 4-carbon (if at least 4 carbon atoms are present in the olefin), in the presence of a solid metallocene catalyst system comprising a bulky ligand transition metal complex component of the stoichiometric Formula 1 and an activator comprising an organoaluminum compound or a hydrocarbylboron compound or a mixture thereof:

  Formula 1 wherein L is the bulky ligand, M is the transition metal, X and X' may be the same or different and are independently selected from the group consisting of halogen, hydrocarbyl group or hydrocarboxyl group having 1–20 carbon atoms, wherein m is 1–3, n is 0–3, p is 0–3 and the sum of the integers m+n+p corresponds to the transition metal valency, to thereby form the aforesaid a viscous oligomer oil product mixture comprising an essentially terminally unsaturated viscous, essentially 1-olefin-containing poly (1-olefin) or copoly (1-olefin) of molecular weight between about 300 and about 10,000 that exhibits a terminal vinylidene content of more than 50%;

wherein the aforesaid solid metallocene catalyst system is formed by a process comprising:

(a) combining at a temperature in the range of from about −40 0° C. to about 150° C. in a an organic solvent boiling from −40 to 250° C. at atmospheric pressure a soluble metallocene and a soluble activator comprising at least one of an organoaluminum and a hydrocarbylboron to form a soluble metallocene- and activator-containing catalyst system as the combination product; and (b) removing the aforesaid solvent to thereby form the aforesaid catalyst system as a solid; and (ii) oligomerizing at least a pre-selected fraction of the viscous oligomer oil product mixture formed in step (i) in the presence of an acidic oligomerization catalyst to thereby form the aforesaid viscous oligomer oil having predetermined properties, wherein the resulting product mixture comprises less than 35% oligomers that contain two or less monomeric units and at least 60% of oligomers that contain at least three monomeric units.

2. The process of claim 1 wherein step (a) is performed at a temperature in the range of from about −40° C. to about 150° C.

3. The process of claim 2 wherein step (a) is performed, at a temperature in the range of from about 0° C. to about 100° C.

4. The process of claim 3 wherein step (a) is performed, at a temperature in the range of from about 20° C. to about 80° C.

5. The process of claim 1 wherein the solvent comprises a $C_4$ to $C_{14}$ hydrocarbon.

6. The process of claim 5 wherein the solvent comprises a halogenated aromatic solvent such as chlorobenzene or an aromatic ether.

7. The process of claim 1 wherein the solvent boils between 0 and 200° C. at 1 atm.

8. The process of claim 7 wherein the solvent boils between 30 and 150° C.

9. The process of claim 1 wherein the solvent is removed in step (b) by evaporation.

10. The process of claim 9 wherein the solvent is removed in step (b) by evaporation under reduced pressure.

11. The process of claim 1 wherein the solvent is removed in step (b) by nitrogen or argon stripping.

12. The process of claim 1 wherein the feed comprises one or more $C_4$ to $C_{20}$ 1-olefin.

13. The process of claim 1 wherein the aforesaid poly(1-olefin) or copoly(1-olefin) produced exhibits a terminal vinylidene content of more than 80%.

14. The process of claim 13 wherein the aforesaid poly (1-olefin) or copoly (1-olefin) exhibits a terminal unsaturation of more than 90%.

15. The process of claim 1, wherein the aforesaid metal complex contains a multiplicity of bonded atoms forming a group which may be cyclic with one or more optional heteroatoms.

16. The process of claim 1 wherein the metallocene is represented by the stoichiometric Formula 2

$(Cp)_m MR^1_n R^2_p$ wherein each Cp is a substituted or unsubstituted cyclopentadienyl or indenyl ring, each such substituent thereon can be the same or different and is an alkyl, alkenyl, aryl, alkaryl, or aralkyl radical having from 1 to 20 carbon atoms or at least two carbon atoms formed together to form a part of a $C_4$ or $C_6$ ring; wherein M is a group IV, V or VI transition metal; wherein $R^1$ and $R^2$ are independently selected from the group consisting of halogen, hydrocarbyl, hydrocarboxyl, each having 1–20 carbon atoms; and wherein m is 1–3, n is 0–3, p is 0–3, and the sum of m+n+p corresponds to the oxidation state of M.

17. The process of claim 16 wherein the metallocene is represented by the Formulas 3 or 4

$(C_5R^3_g)_k R^4_s (C_5R^3_g) MQ_{3-k-x}$  Formula 3

$R^4_s (C_5R^3_g) MQ^1$  Formula 4 wherein each $C_5R^3_g$ is a substituted or unsubstituted cyclopentadienyl and each $R^3$ may be the same or different and is hydrogen, alkyl, alkenyl, alkaryl, aryl, or aralkyl having from 1 to 20 carbon atoms or at least 2 carbon atoms joined together to form a part of a $C_4$ to $C_6$ ring; wherein $R^4$ is either 1) an alkylene radical containing from 1 to 4 carbon atoms, or 2) a dialkyl germanium or silicon or an alkyl phosphoric or amine radical and $R^4$ is substituting on and bridging two $C_5R^3_g$ rings or bridging one $C_5R^3_g$ ring back to M; wherein each Q can be the same or different and is an alkyl, alkenyl, aryl, alkaryl, or arylalkyl radical having from 1 to 20 carbon atoms or halogens, and Q' is an alkylidene radical having from 1 to 20 carbon atoms; when k is 0, x is 1, otherwise x is always 0; and wherein s is 0 or 1; and when s is 0, g is 5 and k is 0, 1 or 2; and when s is 1, g is 4 and k is 1.

18. The process of claim 17 wherein each $C_5R^3_g$ is a mono-substituted cyclopentadienyl of type $C_5H_4R^3$ and each $R^3$ may be the same or different primary or secondary alkyl radical.

19. The process of claim 18 wherein the polymerization is conducted at a temperature of 25–150° C.

20. The process of claim 19 wherein the polymerization product is a low viscosity oil having a viscosity in the range of 2–20 cSt at 100° C.

21. The process of claim 17 wherein each $C_5R^3_g$ is a di, tri, or tetra-substituted cyclopentadienyl of formula $C_5H_3R^3_2$, $C_5H_2R^3_3$, or $C_5HR^3_4$, and each $R^3$ may be the same or different primary or secondary alkyl radical.

22. The process of claim 21 wherein the polymerization is conducted at temperature of 25–150° C.

23. The process of claim 22 wherein the product of the polymerization is a high viscosity oil having a viscosity in the range of 20–5,000 cSt at 100° C.

24. The process of claim 1 wherein the polymerization is conducted under low hydrogen partial pressures.

25. The process of claim 24 wherein the partial pressure of hydrogen in the polymerization is 100 psig or less.

26. The process of claim 25 wherein the partial pressure of hydrogen in the polymerization is 50 psig or less.

27. The process of claim 17 wherein the metal in the aforesaid metal in the complex is a metal of Periodic Group IVB.

28. The process of claim 1 wherein the activator comprises boron trifluoride and a promoter.

29. The process of claim 28 wherein a relatively lower molecular weight fraction of the product from step (i) is separated therefrom and oligomerized in step (ii).

30. The process of claim 29 wherein a fraction comprising the monomeric and dimeric components of the product mixture from the polymerization in step (i) are separated therefrom and oligomerized in step (ii).

31. The process of claim 29 wherein a fraction comprising the dimeric components of the product mixture from the polymerization in step (i) are separated therefrom and oligomerized in step (ii).

32. The process of claim 29 wherein a fraction comprising the dimeric components and a portion of the trimeric components with or without monomeric components of the product mixture from the polymerization in step (i) are separated therefrom and oligomerized in step (ii).

33. The process of claim 28 wherein an admixture of the aforesaid preselected fraction of the product mixture from the polymerization in step (i) and one or more vinyl olefins added from an external source containing from 4 to 20 carbon atoms is oligomerized in step (ii).

34. The process of claim 28 wherein the entire product from the polymerization in step (i) is oligomerized in step (ii).

35. The process of claim 33 wherein 1-decene is polymerized in the polymerization in step (i) and an admixture of the fraction of the product mixture from step (i) containing 20 carbon atoms and less and the aforesaid one or more vinyl olefin is oligomerized in step (ii).

36. The process of claim 35 wherein the aforesaid vinyl olefin in the admixture is 1-dodecene or 1-tetradecene.

37. The process of claim 28 wherein the product mixture from step (ii) comprises at least 65% by weight of oligomers that contain three monomeric units.

38. The process claim 37 wherein the product mixture from step (ii) comprises at least 70% by weight of oligomers that contain three monomeric units.

39. The process of claim 38 wherein the product mixture from step (ii) comprises at least 80% of oligomers that contain three monomeric units.

40. The process of claim 28 wherein the product mixture from step (ii) comprises less than 25% of oligomers that contain one or two monomeric units.

41. The process of claim 40 wherein the product mixture from step (ii) comprises less than 15% of oligomers that contain one or two monomeric units.

42. The process of claim 1 wherein the solid catalyst system and the viscous oligomer oil product mixture from polymerization step (i) are separated.

43. The process of claim 42 wherein the separated solid catalyst system is re-used in polymerization step (i).

* * * * *